(12) United States Patent
Liu et al.

(10) Patent No.: US 11,447,736 B2
(45) Date of Patent: Sep. 20, 2022

(54) CELL SEPARATION APPARATUS FOR BIOREACTOR

(71) Applicant: ALIT BIOTECH (SHANGHAI) CO., LTD., Shanghai (CN)

(72) Inventors: Yu Liu, Shanghai (CN); Rui Chen, Shanghai (CN)

(73) Assignee: ALIT BIOTECH (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 17/478,878

(22) Filed: Sep. 18, 2021

(65) Prior Publication Data
US 2022/0186173 A1 Jun. 16, 2022

Related U.S. Application Data

(63) Continuation of application No. 17/198,291, filed on Mar. 11, 2021.

(30) Foreign Application Priority Data

Dec. 10, 2020 (CN) .......................... 202011434563.3

(51) Int. Cl.
*B01D 53/22* (2006.01)
*C12M 1/00* (2006.01)
(Continued)

(52) U.S. Cl.
CPC ........... *C12M 47/02* (2013.01); *B01D 63/082* (2013.01); *B01D 63/087* (2013.01);
(Continued)

(58) Field of Classification Search
CPC ........... B01D 63/088; B01D 2313/243; B01D 2319/02; B01D 63/087; B01D 2313/086;
(Continued)

(56) References Cited

U.S. PATENT DOCUMENTS 8,163,896 B1 * 4/2012 Bentwich ........... C07K 14/4702
536/24.5
8,207,316 B1 * 6/2012 Bentwich ........... C12N 15/1131
536/23.1
(Continued)

FOREIGN PATENT DOCUMENTS

CN 102553440 A 7/2012
CN 102899241 A 1/2013
(Continued)

OTHER PUBLICATIONS

Wang, Dianliang et al., Development of Mesenchymal Stem Cell Filter Separator, Chinese Medical Equipment Journal, 34(8): 27-28, 2013.
(Continued)

*Primary Examiner* — Anthony R Shumate
(74) *Attorney, Agent, or Firm* — Metis IP LLC

(57) ABSTRACT

The present disclosure provides a cell separation apparatus for a bioreactor. The cell separation apparatus may be disposed outside the bioreactor and in fluid connection with the bioreactor, the cell separation apparatus may be in a shape of a box body, the cell separation apparatus may include a liquid buffer device including a first liquid cavity disposed in the box body; a filter device including a filter channel and a filter membrane disposed in the box body, the filter membrane may be disposed above the filter channel; and a first liquid channel may be configured in the box body to facilitate a fluid communication between the first liquid cavity and the filter channel. A power system for filtering and microfluidic channels are integrated in the cell separation apparatus that is of a box shape, thereby reducing the volume and production cost thereof.

20 Claims, 11 Drawing Sheets

(51) Int. Cl.
  *B01D 69/10* (2006.01)
  *B01D 63/08* (2006.01)
  *B01D 65/10* (2006.01)
  *C12M 1/34* (2006.01)
  *B01D 69/06* (2006.01)

(52) U.S. Cl.
  CPC ........... *B01D 63/088* (2013.01); *B01D 65/10* (2013.01); *B01D 69/06* (2013.01); *B01D 69/10* (2013.01); *C12M 29/00* (2013.01); *C12M 41/40* (2013.01); *B01D 2313/086* (2013.01); *B01D 2313/243* (2013.01); *B01D 2319/02* (2013.01)

(58) Field of Classification Search
  CPC ...... B01D 63/082; B01D 69/06; B01D 69/10; B01D 65/10; C12M 29/00; C12M 47/02; C12M 41/40
  See application file for complete search history.

(56) References Cited

U.S. PATENT DOCUMENTS

| | | | |
|---|---|---|---|
| 2004/0084148 A1* | 5/2004 | Sasaoka | H01J 37/32733 156/345.32 |
| 2004/0115349 A1* | 6/2004 | Sakamoto | H01L 21/02112 427/255.394 |
| 2011/0002812 A1* | 1/2011 | Asogawa | G01N 35/00029 422/68.1 |
| 2011/0076754 A1 | 3/2011 | Frey et al. | |
| 2011/0155667 A1* | 6/2011 | Charest | B01D 63/08 210/651 |
| 2011/0312622 A1* | 12/2011 | Azimi | F16K 99/0036 506/39 |
| 2013/0264286 A1 | 10/2013 | Tai | |
| 2013/0327722 A1 | 12/2013 | Siddiqui et al. | |
| 2014/0360939 A1* | 12/2014 | Yamada | B01D 53/228 210/638 |
| 2015/0041395 A1 | 2/2015 | Oranth et al. | |
| 2016/0158428 A1* | 6/2016 | Charest | A61M 1/3403 210/637 |
| 2016/0313306 A1* | 10/2016 | Ingber | C12M 23/16 |
| 2016/0333295 A1* | 11/2016 | Baker | C12M 33/04 |
| 2018/0071689 A1 | 3/2018 | Xu et al. | |
| 2019/0185803 A1 | 6/2019 | Grant | |
| 2019/0240622 A1 | 8/2019 | Pavlik | |
| 2020/0080045 A1* | 3/2020 | Bernate | C12M 41/40 |
| 2020/0197593 A1* | 6/2020 | Remcho | B01D 63/088 |
| 2020/0215491 A1 | 7/2020 | Takayama et al. | |
| 2020/0231921 A1 | 7/2020 | Zhang et al. | |
| 2020/0397821 A1* | 12/2020 | Frost | C07K 16/2803 |
| 2021/0315496 A1* | 10/2021 | Carvalho de Sousa | A61B 5/150343 |
| 2021/0403853 A1* | 12/2021 | Ludlam | C12M 35/04 |

FOREIGN PATENT DOCUMENTS

| | | |
|---|---|---|
| CN | 205874406 U | 1/2017 |
| CN | 109415673 A | 3/2019 |
| CN | 208776732 U | 4/2019 |
| CN | 110396474 A | 11/2019 |
| CN | 112553054 A | 3/2021 |
| CN | 214881577 U | 11/2021 |
| WO | 2019139842 A1 | 7/2019 |
| WO | 2020173762 A1 | 9/2020 |

OTHER PUBLICATIONS

Marie-Francoise Clincke et al., Very High Density of CHO Cells in Perfusion by ATF or TFF in WAVE BioreactorTM. Part I. Effect of the Cell Density on the Process, Biotechnol. Prog., 29(3): 754-767, 2013.
International Search Report in PCT/CN2021/133865 dated Feb. 28, 2022, 6 pages.
Written Opinion in PCT/CN2021/133865 dated Feb. 28, 2022, 5 pages.
The Second Office Action in Chinese Application No. 202011434563.3 dated Jan. 4, 2022, 21 pages.
Zhu, Yuehai et al., Multilayer Plate Type Membrane Filter, Industrial Water Treatment, 2016, 6 pages.
Lv, Jianxin et al., Sample Filter, Molecular Diagnostics, 2010, 5 pages.

\* cited by examiner

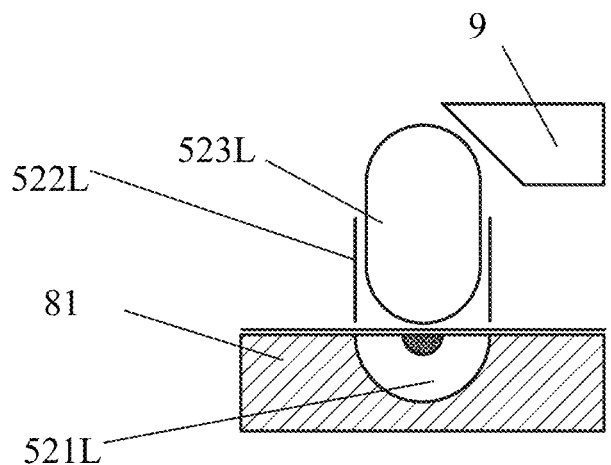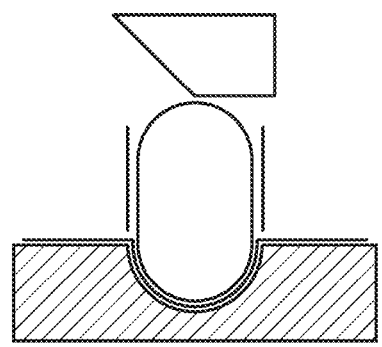
FIG. 5A　　　　　　　FIG. 5B
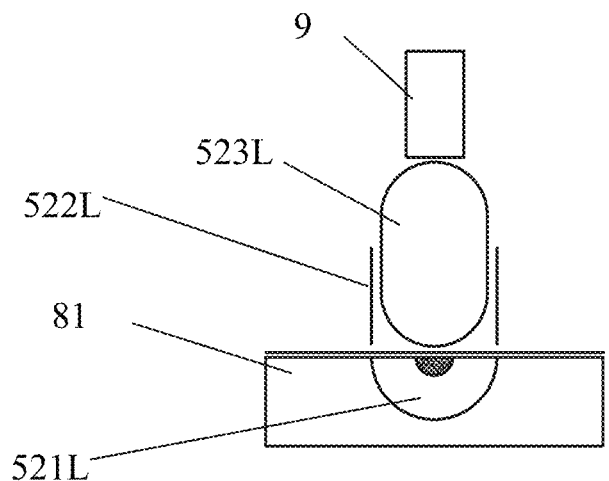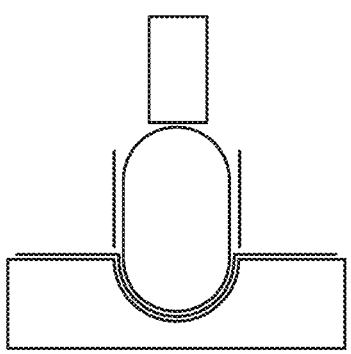
FIG. 6A　　　　　　　FIG. 6B

CELL SEPARATION APPARATUS FOR BIOREACTOR

CROSS-REFERENCE TO RELATED APPLICATIONS

This application is a continuation of U.S. patent application Ser. No. 17/198,291, filed Mar. 11, 2021, which claims priority of Chinese Patent Application No. 202011434563.3, filed on Dec. 10, 2020, the contents of which are hereby incorporated by reference.

TECHNICAL FIELD

The present disclosure generally relates to the field of bioreactors, and in particular, to a cell separation apparatus for a bioreactor.

BACKGROUND

In a design of animal cell bioreactors, more and more processes involve a separation of cells from a culture fluid or other solutions. These processes include perfusion culturing, fluid exchanging or cell cleaning. Traditional separation apparatuses include an alternating tangential flow filtration (ATF) system, a tangential flow filtration (TFF) system, etc. These systems use a centrifugal pump or a diaphragm pump to provide power and pump a mixture of cells and a culture fluid to a hollow fiber column, and use fiber pores of the hollow fiber column to separate cells and the culture fluid.

Some systems use a centrifugal pump to provide power for pumping the mixture of cells and the culture fluid. However, the centrifugal pump has a disadvantage of, for example, an excessive shear force. Animal cells (especially human T cells or stem cells) are very sensitive to the shear force. An excessive shear force may cause the oncogenesis of stem cells or loss of cell markers, thereby seriously affecting the safety of cell therapy products. Some systems use a diaphragm pump to provide power for pumping the mixture of cells and the culture fluid. However, the diaphragm pump has a disadvantage of, for example, non-linear pressurization of liquid in pipeline. Non-linear pressurization can lead to a relatively large fluctuation of an instantaneous pressure in a culture system, which brings one or more potential effects to the stability of the process.

In actual use of bioreactors, the hollow fiber column used for the separation of cells and culture fluids is not only expensive, but also too large (e.g., for the ATF2 system of XCell™, a 2 L-10 L bioreactor requires a 60 cm high hollow fiber column), and thus is not suitable for small disposable cell separation apparatuses. In addition, multiple pipe connections are required between the hollow fiber column and the bioreactor, and accordingly, assembly and disassembly operations thereof are complicated.

SUMMARY

According to an aspect of the present disclosure, a cell separation apparatus that can overcome at least one defect in the prior art is provided.

The subject technology of the present disclosure is explained in terms of various aspects described below. For convenience, various examples of various aspects of the subject technology are described as labeled terms (1, 2, 3 etc.). These terms are provided as examples, rather than limiting the subject technology of this disclosure.

In one aspect of the present disclosure, a cell separation apparatus for a bioreactor is provided. The cell separation apparatus may be disposed outside the bioreactor and in fluid connection with the bioreactor, the cell separation apparatus may be in a shape of a box body, the cell separation apparatus may comprise.

a liquid buffer device including a first liquid cavity disposed in the box body; and a filter device including a filter channel and a filter membrane disposed in the box body, the filter membrane being disposed above the filter channel.

wherein a first liquid channel may be configured in the box body to facilitate a fluid communication between the first liquid cavity and the filter channel.

In some embodiments, the cell separation apparatus may further comprise a power device fixed to the box body, and the first liquid cavity may be in gaseous communication with the power device.

In some embodiments, the power device may include a syringe pump or an air cylinder.

In some embodiments, a volume of the first liquid cavity may be 0.01-0.8 bioreactor culture volume.

In some embodiments, the box body may include a stacked layer, and the stacked layer may include a first shell plate, a membrane layer, a support plate, and a second shell plate.

In some embodiments, the first liquid cavity may be fixed to an outer end surface of the stacked layer.

In some embodiments, the first liquid channel may be recessed from an inner surface of the first shell plate, and a top of the first liquid channel may be covered and sealed by a sealing film in the membrane layer.

In some embodiments, a pressure sensor may be configured in the first liquid channel to monitor a clogging state of the filter device.

In some embodiments, the first liquid channel may be configured on the first shell plate through at least one of machining, laser etching, or soft plastic injection molding.

In some embodiments, a cross section of the first liquid channel perpendicular to the first shell plate may be of a shape of a semicircle or rectangle, and a diameter or a side length of the first liquid channel may be in a range from 0.01 mm to 2 mm.

In some embodiments, a diameter or a side length of the first liquid channel may be in a range from 0.1 mm to 1 mm.

In some embodiments, the liquid buffer device may further comprise a second liquid cavity disposed in the box body, a second liquid channel may be disposed in the box body to facilitate a fluid communication between the second liquid cavity and the filter channel.

In some embodiments, the second liquid cavity may be fixed to an outer end surface of the stacked layer.

In some embodiments, the second liquid cavity may be in gaseous communication with the power device.

In some embodiments, a volume of the second liquid cavity may be 0.01-0.8 bioreactor culture volume.

In some embodiments, a third liquid channel may be configured in the box body to facilitate a fluid communication between the first liquid cavity and the bioreactor, and a fourth liquid channel may be configured in the box body to facilitate a fluid communication between the second liquid cavity and the bioreactor.

In some embodiments, the first liquid channel, the second liquid channel, the third liquid channel, and the fourth liquid channel may be recessed from an inner surface of the first shell, and a top of the first liquid channel, a top of the second liquid channel, a top of the third liquid channel, and a top of the fourth liquid channel may be covered and sealed by a sealing film in the membrane layer.

In some embodiments, one or more pressure sensors may be configured in the first liquid channel and/or the third liquid channel to monitor a clogging state of the filter device.

In some embodiments, the first liquid channel, the second liquid channel, the third liquid channel, and/or the fourth liquid channel may be configured on the first shell plate through at least one of machining, laser etching, or soft plastic injection molding.

In some embodiments, a cross section perpendicular to the first shell plate of the first liquid channel, the second liquid channel, the third liquid channel, and/or the fourth liquid channel may be of a shape of a semicircle or rectangle, and a diameter or a side length of the first liquid channel, the second liquid channel, the third liquid channel, and/or the fourth liquid channel may be in a range from 0.01 mm to 2 mm.

In some embodiments, a diameter or a side length of the first liquid channel, the second liquid channel, the third liquid channel, and/or the fourth liquid channel may be in a range from 0.1 mm to 1 mm.

In some embodiments, the first liquid channel, the second liquid channel, the third liquid channel, and the fourth liquid channel may be equipped with a valve.

In some embodiments, the value may include a valve body cavity and a spool cavity that are in fluid communication, and the valve body cavity may be disposed in a corresponding liquid channel.

In some embodiments, the valve body cavity may be recessed from an inner surface of the first shell plate, and a top of the valve body cavity may be covered and sealed by a sealing film in the membrane layer.

In some embodiments, a cross section of the valve body cavity perpendicular to the first shell plate may be larger than a cross section of a corresponding liquid channel.

In some embodiments, a cross section of the valve body cavity perpendicular to the first shell plate may be of a circular, oval, square, or rectangular shape.

In some embodiments, the valve body cavity may be configured on the first shell plate through at least one of machining, laser etching, or soft plastic injection molding.

In some embodiments, the spool cavity may be a through cavity disposed on the support plate and the second shell plate, and the position of the spool cavity may correspond to the valve body cavity.

In some embodiments, the cell separation apparatus may further include an additional power device fixed to the box body, and the spool cavity may be in fluid communication with the additional power device.

In some embodiments, the additional power device may be configured to push the gas into the spool cavity to generate a positive pressure in the spool cavity, and make the sealing film seal the valve body cavity to close a corresponding liquid channel. The additional power device may be further configured to suction the gas out from the spool cavity to generate a negative pressure in the spool cavity, and make the sealing film release the valve body cavity to open the corresponding liquid channel.

In some embodiments, the additional power device may be configured to push the spool into the valve body cavity, and make the sealing film seal the valve body cavity to close a corresponding liquid channel. The additional power device may be further configured to push the spool to leave the valve body cavity, and make the sealing film release the valve body cavity to open the corresponding liquid channel.

In some embodiments, the filter channel may be recessed from an inner surface of the first shell plate, and a top of the filter channel may be covered by the filter membrane in the membrane layer.

In some embodiments, the filter channel may be configured on the first shell plate through at least one of machining, laser etching, or soft plastic injection molding.

In some embodiments, a cross section of the filter channel perpendicular to the first shell plate may be of a shape of a semicircle or rectangle, and a diameter or a side length of the filter channel may be in a range from 0.01 mm to 2 mm.

In some embodiments, a diameter or a side length of the filter channel may be in a range from 0.1 mm to 1 mm.

In some embodiments, an arrangement pattern of the filter channel on the first shell plate may be of a coiled shape.

In some embodiments, the filter channel may be configured as a single filter channel, and an outlet of the single filter channel may be closed or the single filter channel may form a closed loop.

In some embodiment, the filtering channel may be configured as a plurality of filter channels connected in parallel, and an outlet of each filter channel of the plurality of filter channels may be closed or the each filter channel may form a closed loop.

In some embodiments, each filter channel of the plurality of filter channels may be equipped with a valve.

In some embodiments, the filter membrane may be configured as a single layer or stacked multiple layers.

In some embodiments, the filter membrane may be made of a material including PTFE, PP, PC, nylon, PES, PVDF, or a sintered porous material.

In some embodiments, the filter membrane may adopt a pore size of 0.2 µm, 1 µm, 4 µm, 5 µm, 10 µm, 20 µm, 50 µm, and/or 200 µm.

In some embodiments, the filter membrane may be supported by the support plate to increase the strength of the filter membrane when the liquid presses the filter membrane.

In some embodiments, the support plate may be made of a material including PS, PMMA, PETG, or PET.

In some embodiments, the filter device may further include a collection chamber configured to collect the liquid flowing through the filter membrane.

In some embodiments, the support plate may be equipped with a plurality of through holes on a site corresponding to the filter channel, the collection chamber may be recessed from an inner surface of the second shell plate, and a position of the collection chamber corresponds to the plurality of through holes on the support plate.

In some embodiments, the collection chamber may be connected to the outside of the cell separation apparatus through a return conduit.

In some embodiments, a peristaltic pump or a pinch valve may be disposed on the return conduit to control a flow rate of the liquid backwashing the filter membrane.

In some embodiments, a length of the box body may be in a range from 1 cm to 8 cm, a width of the box body may be in a range from 1 cm to 15 cm, and a height of the box body may be in a range from 1 cm to 15 cm.

In some embodiments, the first liquid cavity and the second liquid cavity may be configured such that when a valve of the third liquid channel is open and a valve of the first liquid channel is closed, a gas can be suctioned from the first liquid cavity, and thus, the liquid in the bioreactor may be suctioned to the first liquid cavity through the third liquid channel. When a valve of the fourth liquid channel is closed and a valve of the second liquid channel is open, the gas can be suctioned to the second liquid cavity, and thus, the liquid in the second liquid cavity may leave the second liquid cavity, and be pushed to the filter device through the second liquid channel.

In some embodiments, the first liquid cavity and the second liquid cavity may be configured such that when a valve of the third liquid channel is closed and a valve of the first liquid channel is open, a gas can be pushed to the first liquid cavity, and thus, the liquid in the first liquid cavity may leave the first liquid cavity, and be pushed to the filter device through the first liquid channel. When a valve of the fourth liquid channel is open and a valve of the second liquid channel is closed, the gas can be suctioned from the second liquid cavity, and thus, the liquid in the bioreactor may be suctioned to the second liquid cavity through the fourth liquid channel.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

It should be understood that the foregoing general description and the following detailed description are both exemplary and illustrative, and are intended to provide a further description of the subject technology of the claimed disclosure.

BRIEF DESCRIPTION OF THE DRAWINGS

Based on the following specific embodiments and the drawings, various aspects of the present disclosure will be better understood. In the drawings:

FIGS. 5A and 5B are schematic diagrams illustrating an example of a valve of the disposable cell separation apparatus shown in FIG. 2;

FIGS. 6A and 6B are schematic diagrams illustrating another example of the valve of the disposable cell separation apparatus shown in FIG. 2;

DETAILED DESCRIPTION

Figure 1:
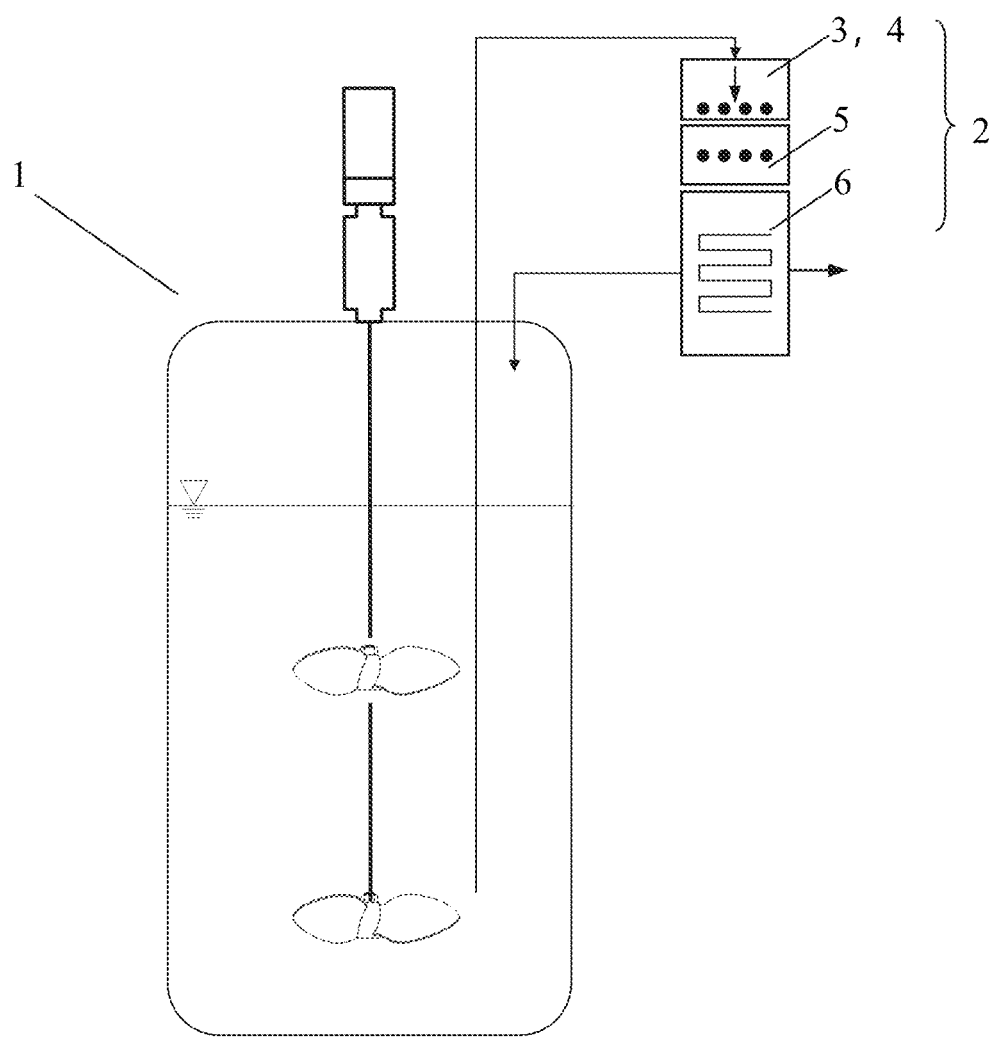
FIG. 1 is a schematic diagram illustrating a disposable cell separation apparatus.

The present disclosure will be described below with reference to the accompanying drawings, in which the drawings illustrate several embodiments of the present disclosure. However, it should be understood that the present disclosure can be presented in many different ways, and is not limited to the embodiments described below. In fact, the embodiments described below are intended to make the disclosure of the present disclosure more complete and fully explain the protection scope of the present disclosure to those skilled in the art. It should also be understood that the embodiments disclosed herein can be combined in various ways to provide more additional embodiments.

It should be understood that in all the drawings, the same reference numerals denote the same elements. In the drawings, the dimensions of certain features may be deformed for clarity.

It should be understood that the terms in the specification are only used to describe specific embodiments and are not intended to limit the present disclosure. Unless otherwise defined, all terms (including technical terms and scientific terms) used in the specification have the meanings commonly understood by those skilled in the art. For brevity and/or clarity, well-known functions or structures may not be described in detail.

The singular forms "a", "the" and "this" used in the specification include plural forms unless clearly indicated. The terms "including", "comprising" and "containing" used in the specification indicate the presence of the claimed feature, but do not exclude the presence of one or more other features. The term "and/or" used in the specification includes any and all combinations of one or more of the related listed items. The terms "between X and Y" and "between about X and Y" used in the specification should be interpreted as including X and Y. The term "between about X and Y" used in this specification means "between about X and about Y", and the term "from about X to Y" used in this specification means "from about X to about Y".

In the specification, when an element is referred to as being "on", "attached" to another element, "connected" to another element, "coupled" to another element, or "contacting" another element, etc., the element may be directly on another element, attached to another element, connected to another element, coupled to another element, or contacting another element, or an intermediate element may be present. In contrast, it is said that an element is "directly on" another element, "directly attached" to another element, "directly connected" to another element, "directly coupled" to another element, or "directly contacting" another element, there will be no intermediate element. In the specification, when an element is arranged "adjacent" to another element, it may mean that the element has a portion overlapping with an adjacent element or a portion located above or below the adjacent element.

In the specification, terms such as "upper", "lower", "left", "right", "front", "rear", "high", "low", etc., can describe the relationship of one element and another element in the drawings. It should be understood that, in addition to the orientation shown in the drawings, the terms describing spatial relationships also indicate different orientations of the device in use or operation. For example, when the device in the drawings is turned upside down, elements that were originally described as being "below" other elements may now be described as being "above" other elements. The device can also be oriented in other ways (e.g., rotated by 90 degrees or in other orientations), and the relative spatial relationships will be explained accordingly.

FIG. 1 is a schematic diagram illustrating a disposable cell separation apparatus 2. The cell separation apparatus 2 may be configured to separate or remove specific constituent components (such as cells) of a liquid (such as a culture fluid) in the bioreactor 1. As shown in the figure, the cell separation apparatus 2 may include a power device 3, a liquid buffer device 4, a valve device 5, and a filter device 6. The liquid buffer device 4 and the bioreactor 1, the filter device 6 and the bioreactor 1, and the liquid buffer device 4 and the filter device 6 may be in fluid connection via liquid pipelines. The power device 3 and the liquid buffer device 4 may be in fluid connection via a gas pipeline. The power device 3 may be configured to drive the liquid to leave the bioreactor 1, and enter the liquid buffer device 4 and the filter device 6, and finally be discharged. The liquid buffer device 4 may be configured to temporarily receive the liquid leaving the bioreactor 1, so that the liquid in the entire flow path flows smoothly without generating back and forth pressure fluctuations. The valve device 5 may be configured to control the opening and closing of the liquid pipelines. The filter device 6 may be configured to separate, for example, cells and culture fluids.

Figure 2:
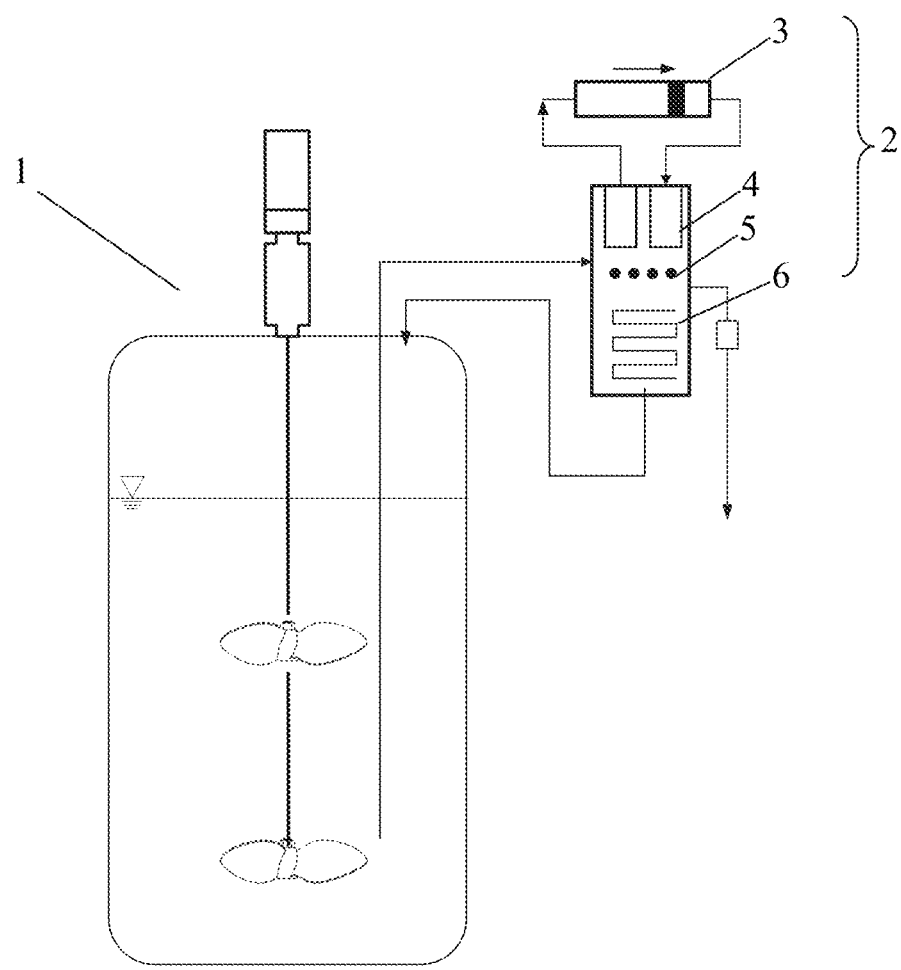
FIG. 2 is a schematic diagram illustrating usage of the disposable cell separation apparatus according to a first embodiment of the present disclosure.
Figure 3A:
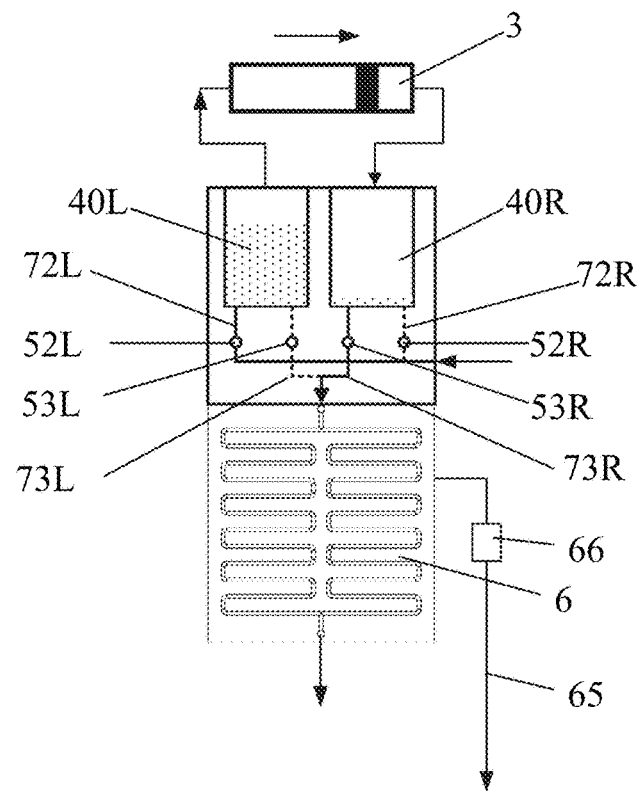
FIGS. 3A and 3B are schematic diagrams illustrating connections of components of the disposable cell separation apparatus shown in FIG. 2.
Figure 3B:
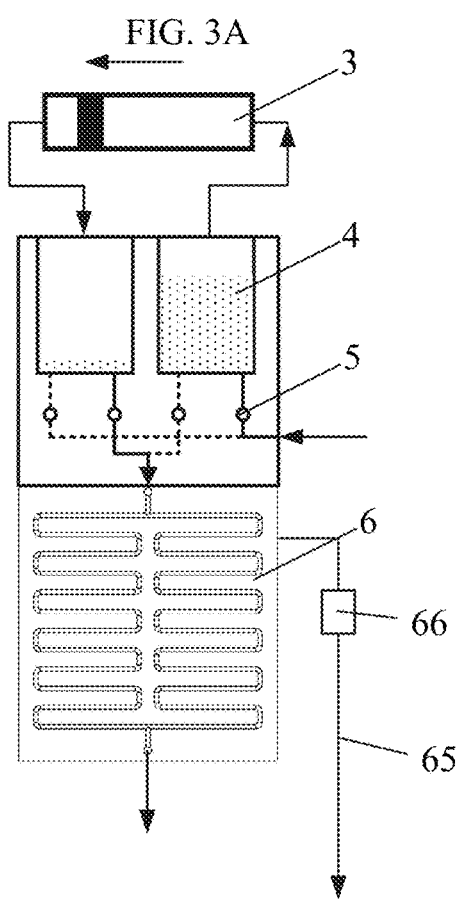
Figure 4A:
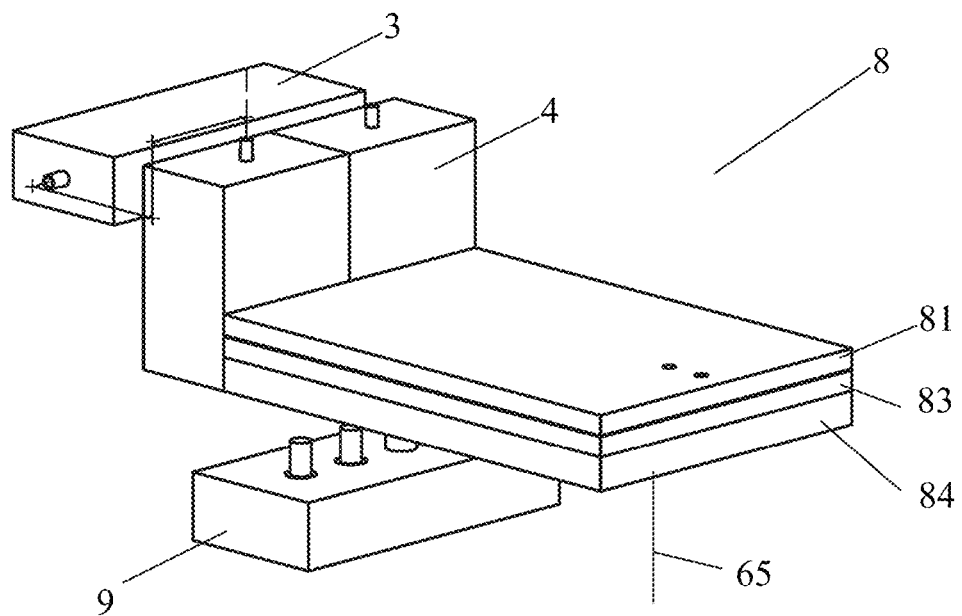
FIGS. 4A and 4B show an exploded stereogram and an exploded perspective view illustrating the disposable cell separation apparatus shown in FIG. 2.
Figure 4B:
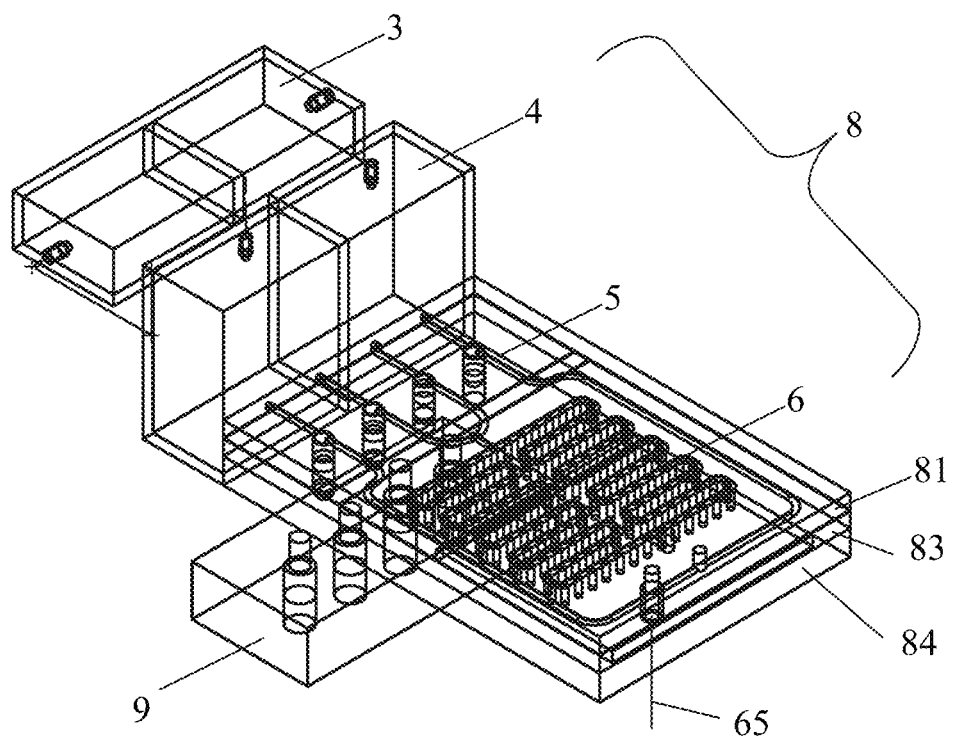
Figure 4C:
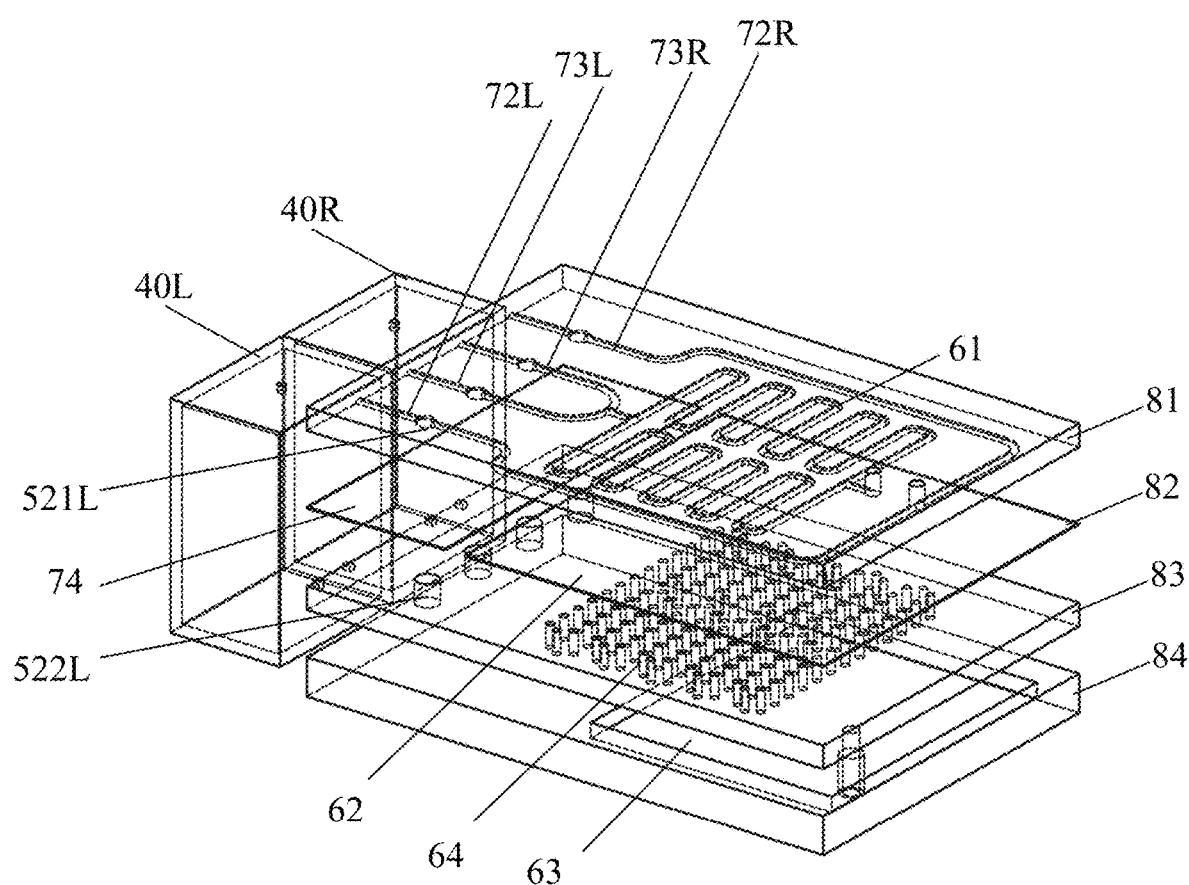
FIG. 4C is an exploded perspective view illustrating the disposable cell separation apparatus without related power device.

FIG. 2 is a schematic diagram illustrating usage of the disposable cell separation apparatus 2 according to a first embodiment of the present disclosure, FIGS. 3A and 3B are schematic diagrams illustrating connections of components of the disposable cell separation apparatus 2, and FIGS. 4A and 4B show an exploded stereogram and an exploded perspective view illustrating the disposable cell separation apparatus 2, and FIG. 4C is an exploded perspective view illustrating the disposable cell separation apparatus 2 without related power device. As shown in the figure, the liquid buffer device 4, the valve device 5 and the filter device 6 may be integrated in the box body 8 and arranged from a first end of the box body 8 to an opposite second end. The liquid buffer device 4 and the filter device 6 may be connected by a liquid pipeline disposed in the box body 8, and the valve device 5 may be disposed in the liquid pipeline. The power device 3 may be fixed to the first end of the box body 8 by various known methods (such as screw connection, welding, shape fitting, etc.), and in fluid connection with the liquid buffer device 4. The length of the box body 8 from the first end to the second end may be in a range from 1 cm to 8 cm, the width may be in a range from 1 cm to 15 cm, and the height may be in a range from 1 cm to 15 cm.

The liquid buffer device 4 may include two side-by-side liquid cavities 40L and 40R disposed near the first end of the box body 8. Each of the liquid cavities 40L and 40R may receive liquid inside the cavity. In some embodiments, each of the liquid cavities 40L and 40R may be of a rectangular or a cube shape, and include an inner wall facing the valve device 5 and the filter device 6, an opposite outer wall, and a side wall connecting the inner wall and the outer wall. The liquid cavity 40L may include air holes disposed on the side wall or the outer wall, and a liquid inlet and an outlet disposed on the inner wall. The air holes may be in fluid communication with the power device 3, the liquid inlet may be in fluid communication with the bioreactor 1 through a liquid channel 72L disposed on the box body 8 and a separate liquid conduit (not shown). The liquid outlet may be in fluid communication with the filter device 6 through a liquid channel 73L disposed on the box body 8.

The power device 3 may be a device capable of driving gas to reciprocate, including, for example, a syringe pump, an air cylinder, or the like. Gas (for example, the air) may exist between the power device 3 and the liquid surface inside the liquid cavity 40L. The power device 3 may pump gas out of the liquid cavity 40L through the air holes of the liquid cavity 40L, and generate a negative pressure in the liquid cavity 40L, thereby pumping the liquid in the bioreactor 1 into the liquid cavity 40L through the separate liquid conduit, the liquid channel 72L, and the liquid inlet. The power device 3 may further push the gas into the liquid cavity 40L through the air holes of the liquid cavity 40L, and generate a positive pressure in the liquid cavity 40L, thereby pushing the liquid in the liquid cavity 40L to the filter device 6 through the liquid outlet and the liquid channel 73L to perform filtering. The power device 3 may use gas to generate a driving force and a drain force, thereby greatly reducing the damage to cells caused by other methods (such as peristaltic pumps or centrifugal pumps). Studies have shown that if the peristaltic pump circulates for more than 30 hours, the cell viability may decrease significantly.

The structure and function of the liquid cavity 40R may be substantially the same as or similar to those of the liquid cavity 40L, and correspondingly, the liquid cavity 40R may include one or more air holes, a liquid inlet and a liquid outlet. The air hole(s) may be in fluid communication with the power device 3, the liquid inlet may be in fluid communication with the bioreactor 1 through a liquid channel 72R disposed on the box body 8 and a separate liquid conduit (not shown), and the liquid outlet may be in fluid communication with the filter device 6 through a liquid channel 73R disposed on the box body 8. Similarly, the power device 3 may push the liquid of the bioreactor 1 into the liquid cavity 40R and out of the liquid cavity 40R using gas.

The volumes of the liquid cavities 40L and 40R may be determined based on a flow rate of the filter device 6, and may generally be 0.01-0.8 bioreactor culture volume. Maximum liquid volumes in the liquid cavities 40L and 40R may account for 40%-80% volume of the liquid cavity to ensure a certain buffering and prevent the liquid from contacting the downstream filter device 6 when the liquid is suctioned. In some embodiments, a liquid level sensor may be installed in the liquid cavities 40L and 40R to determine the action time of the positive pressure and the negative pressure.

In addition to the liquid cavities 40L and 40R, the box body 8 may further include a first shell plate 81, a membrane layer 82, a support plate 83, and a second shell plate 84 that stack on each other. The liquid channels 72L, 73L, 72R, 73R, the valve device 5, and the filter device 6 may be disposed between the stacked layer. The liquid cavities 40L and 40R may be fixed to an outer end surface of the stacked layer in various ways (for example, by ultrasonic welding, bonding, etc.).

The liquid channels 72L, 73L, 72R, and 73R may be configured as micro channels, and may be recessed from an inner surface of the first shell plate 81, and a top of the liquid channels 72L, 73L, 72R, and 73R may be covered and sealed by a sealing film 74 in the membrane layer 82. The inlets of the liquid channels 72L and 72R may be exposed on a side wall of the box body 8, or configured as through holes on the support plate 83 and the second shell plate 84, and in fluid communication with the bioreactor 1 through one or more liquid conduits, and the outlets of the liquid channels 72L and 72R may be respectively connected to the liquid inlet of the cavity 40L and the liquid inlet of the liquid cavity 40R. The inlets of the liquid channels 73L and 73R may be respectively aligned and connected to the outlet of the liquid cavity 40L and the outlet of the liquid cavity 40R, and the outlets of the liquid channels 73L and 73R may be in fluid connection with the filter device 6. In some embodiments, the liquid channels 72L, 73L, 72R, and 73R may be configured on the first shell plate 81 by machining, laser etching, soft plastic injection molding, or the like. In some embodiments, a cross section (that is perpendicular to the first shell plate 81) of the liquid channels 72L, 73L, 72R, 73R may be of a shape of a semicircle or rectangle, and a diameter or a side length of the liquid channels may be in a range from 0.01 mm to 2 mm, and more particularly from 0.1 mm to 1 mm. In some embodiments, one or more pressure sensors may be installed in the liquid channels 72L, 73L, 72R, and 73R to monitor whether the filter device 6 is clogged.

The valve device 5 may be configured to control opening and closing of the liquid channels. As shown in the figure, for the liquid cavity 40L, the valve device 5 may include an inlet valve 52L disposed in the liquid channel 72L, and an outlet valve 53L disposed in the liquid channel 73L. When the power device 3 pumps the gas out from the liquid cavity 40L, the inlet valve 52L may be opened and the outlet valve 53L may be closed, so that the liquid in the bioreactor 1 is suctioned into the liquid cavity 40L through the liquid channel 72L. When the power device 3 pushes the gas into the liquid cavity 40L, the inlet valve 52L may be closed and the outlet valve 53L may be opened, so that the liquid in the liquid cavity 40L is pushed to the filter device 6 through the liquid channel 73L for filtering.

Similarly, for the liquid cavity 40R, the valve device 5 may include an inlet valve 52R disposed in the liquid channel 72R, and an outlet valve 53R disposed in the liquid channel 73R. When the power device 3 pumps the gas out from the liquid cavity 40R, the inlet valve 52R may be opened and the outlet valve 53R may be closed, so that the liquid in the bioreactor 1 is suctioned into the liquid cavity 40R through the liquid channel 72R. When the power device 3 pushes the gas into the liquid cavity 40R, the inlet valve 52R may be closed and the outlet valve 53R may be opened, so that the liquid in the liquid cavity 40R is pushed to the filter device 6 through the liquid channel 73R for filtering.

The structures of the inlet valve 52L, the outlet valve 53L, the inlet valve 52R and the outlet valve 53R may be substantially the same or similar. In the following descriptions, the inlet valve 52L is taken as an example to illustrate the structure of the valve, but it should be understood that the same or similar structure is also applicable to the outlet valve 53L, the inlet valve 52R, and the outlet valve 53R. The inlet valve 52L may include a valve body cavity 521L and a spool cavity 522L. The valve body cavity 521L may be disposed in the liquid channel 72L. Similar to the structure of the liquid channel 72L, the valve body cavity 521L may be recessed from an inner surface of the first shell plate 81, and a top of the valve body cavity 521L may be covered and sealed by the sealing film 74 in the membrane layer 82. In some embodiments, a cross section of the valve body cavity 521L perpendicular to the first shell plate 81 may be larger than a cross section of the liquid channel 72L. The cross section of the valve body cavity 521L along a direction perpendicular to the first shell plate 81 may be of a circular, oval, square, rectangular, or any suitable shape. In some embodiments, the valve body cavity 521L may be configured on the first shell plate 81 by machining, laser etching, soft rubber injection molding, or the like. The spool cavity 522L may be a through cavity disposed on the support plate 83 and the second shell plate 84, and the position of the spool cavity 522L may correspond to the valve body cavity 521L. The power device 9 (for example, an air cylinder, etc.) may be in fluid communication with the spool cavity 522L. The power device 9 may push gas into the spool cavity 522L, and generate a positive pressure in the spool cavity 522L, thereby pushing the sealing film 74 to seal the valve body cavity 521L and close the liquid channel 72L. The power device 9 may further suction gas out from the spool cavity 522L, and generate a negative pressure in the spool cavity 522L, thereby causing the sealing film 74 to release the valve body cavity 521L to open the liquid channel 72L. The power device 9 may be fixed to the box body 8 (for example, the second shell plate 84 of the box body 8) by various known methods (such as screw connection, welding, shape matching, etc.).

In some embodiments, as shown in FIGS. 5A and 5B, and FIGS. 6A and 6B, a spool 523L may be disposed in the spool cavity 522L, and may be driven by the power device 9 to reciprocate into and out of the valve body cavity 521L. The spool 523L may be of a substantially cylindrical shape or a capsule shape. When the spool 523L enters the valve body cavity 521L, the valve body cavity 521L may be closed to close the liquid channel 72L; when the spool 523L leaves the valve body cavity 521L, the valve body cavity 521L may be released to open the liquid channel 72L.

Referring back to FIGS. 2 to 4C, the filter device 6 may include a filter channel 61, a filter membrane 62 and a collection chamber 63. An inlet of the filter channel 61 may be in fluid connection with a confluence of the liquid channels 73L and 73R to receive, from the liquid cavities 40L and 40R, at different times, the liquid to be filtered, and an outlet of the filter channel 61 may be closed or the filter channel 61 may form a closed loop. Similar to the liquid channels 72L, 73L, 72R, 73R, the filter channel 61 may be configured as a microfluidic channel and recessed from an inner surface of the first shell plate 81 and a top of the filter channel 61 may be covered by the filter membrane 62 in the membrane layer 82. In some embodiments, the filter channel 61 may be configured on the first shell plate 81 by mechanical processing, laser etching, soft plastic injection molding, or the like.

In some embodiments, a cross section (that is perpendicular to the first shell plate 81) of the filter channel 61 may be of a semicircular or rectangular shape, and a diameter or a side length of the filter channel may be in a range from 0.01 mm to 2 mm, and more particularly from 0.1 mm to 1 mm, to match the flow rate of the liquid. Because the diameter of the filter channel 61 is relatively small, and the filter channel 61 is relatively long and narrow, the liquid in the filter channel 61 may be in a laminar high-speed flow state (the flow rate is, for example, 2 cm/s-100 cm/s), and the filter membrane 62 may be flushed, thereby effectively improving the service life of the filter membrane 62. Because the filtration direction is perpendicular to the liquid flow direction, a tangential flow filtration may be provided.

Figure 7A:
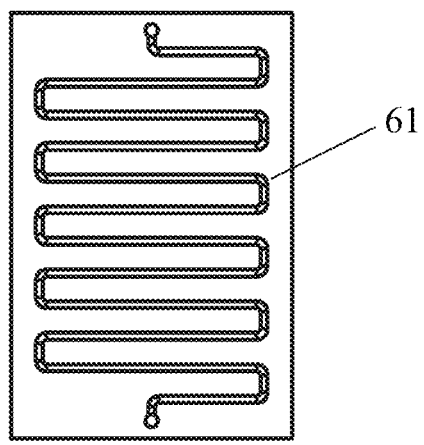
FIGS. 7A-7C are schematic diagrams illustrating filter channels of various layout patterns of the filter device of the disposable cell separation apparatus shown in FIG. 2.
Figure 7B:
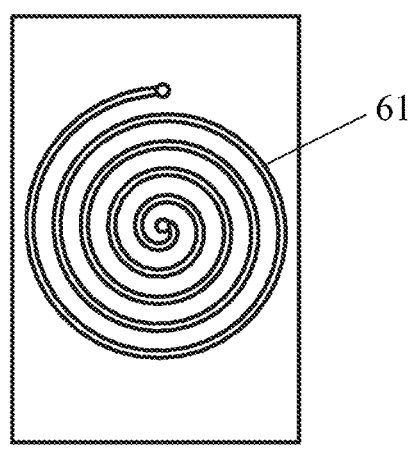
Figure 7C:
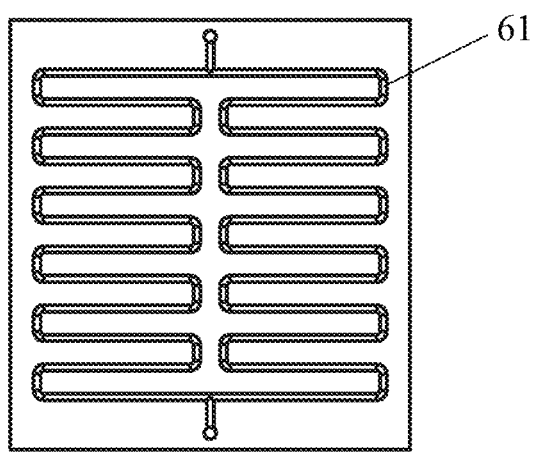

As shown in FIGS. 7A-7C, an arrangement pattern of the filter channel 61 on the first shell plate 81 may be designed into various forms. In some embodiments, the pattern of the filter channel 61 may be of a coiled shape to make full use of the area of the filter membrane 62. Taking liquid resistance factor into account, a length of a single filter channel 61 may be in a range from 20 cm to 1000 cm, and more particularly, from 10 cm to 50 cm.

Figure 8:
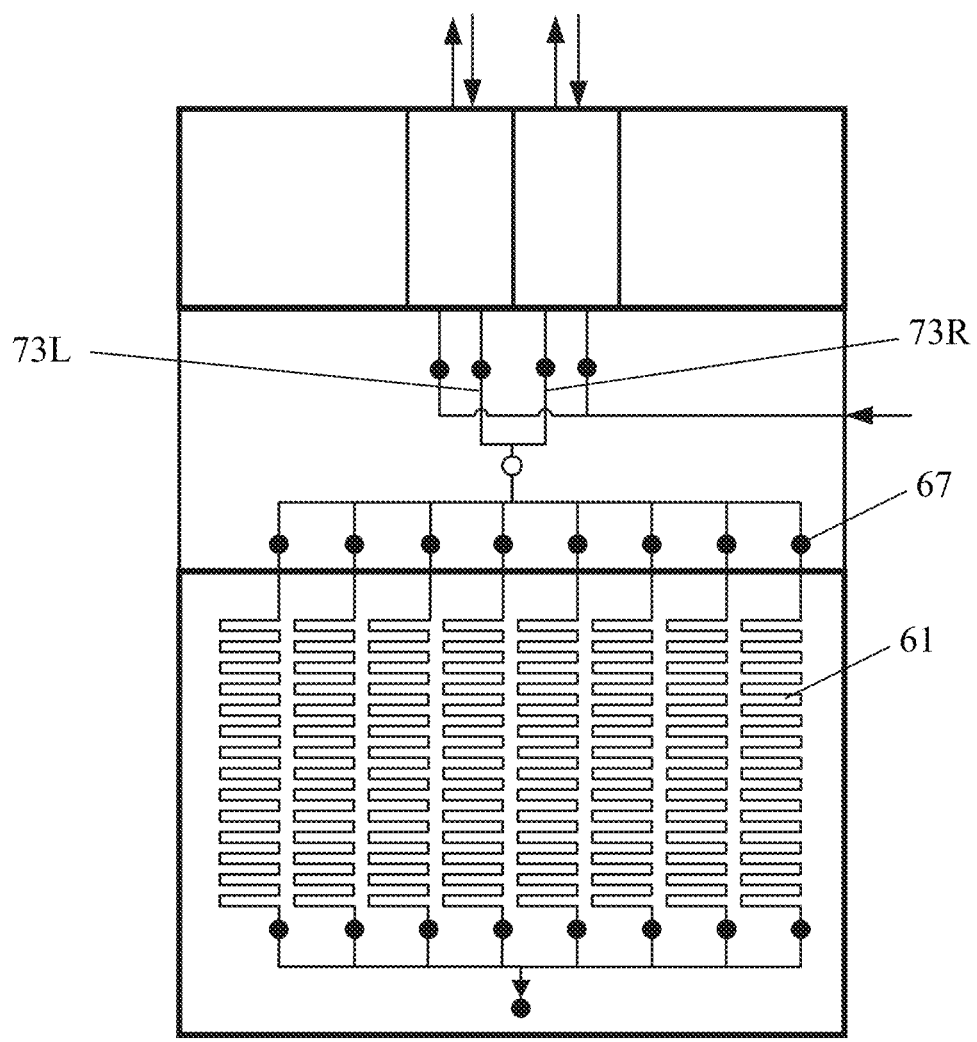
FIG. 8 is a schematic diagram illustrating filter channels in parallel of the filter device of the disposable cell separation apparatus shown in FIG. 2.

In some embodiments, as shown in FIG. 8, the filter channel 61 may be configured as a plurality of filter channels connected in parallel, and the main inlet of the parallel filter channels 61 may be connected to the confluence of the liquid channels 73L and 73R, and the outlet of the parallel filter channels 61 may be closed or the parallel filter channels 61 may form a closed loop. Each filter channel 61 may be equipped with a filter valve 67 to coordinate to open or close the filter channel 61. In a perfusion production process, the filter valves 67 may be opened one by one or opened simultaneously in accordance with different processes, and the requirements of liquid exchange volume and culture time. The structures of the filter valve 67 and the inlet valve 52L may be substantially the same, and the description will not be repeated herein.

Figure 9A:
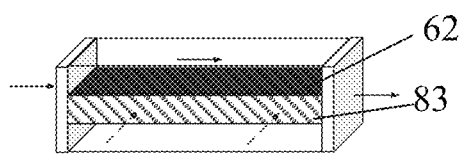
FIGS. 9A and 9B are schematic diagrams illustrating a single layer filter membrane and multilayer filter membrane of the filter device of the disposable cell separation apparatus shown in FIG. 2.
Figure 9B:
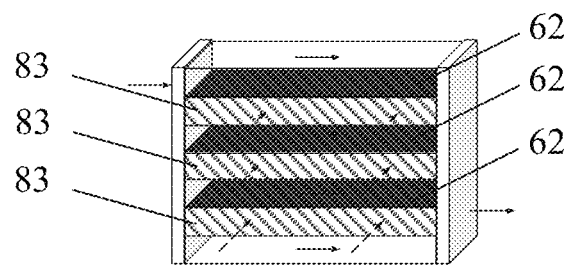

Referring back to FIGS. 2 to 4C, the filter membrane 62 may be supported by the support plate 83 to increase the strength of the filter membrane 62 when the liquid presses the filter membrane 62. The support plate 83 may be equipped with a plurality of through holes 64 on a site corresponding to the filter channel 61, and thus, the filtered liquid can flow into the collection chamber 63 disposed on the second shell plate 84 through the through holes 64 on the support plate 83. As shown in FIGS. 9A and 9B, the filter membrane 62 may be configured as a single layer or multiple layers. In some embodiments, the filter membrane 62 may be configured as multiple layers, each layer of the filter membrane may be supported by a support plate 83, and each layer of the filter membrane may have corresponding micro flow channel, thereby increasing the filtration capacity and making it suitable for a relatively large volume tank.

Referring back to FIGS. 2 to 4C, the collection chamber 63 may be recessed from an inner surface of the second shell plate 84, and the position of the collection chamber 63 may correspond to a plurality of through holes 64 on the support plate 83. The collection chamber 63 may be equipped with a liquid outlet open to the outside of the second shell plate 84, and the liquid may be discharged through a return conduit 65. Thus, the filtered liquid in the collection chamber 63 may be discharged from the culture system. In some embodiments, a peristaltic pump or a pinch valve 66 may be disposed on the return conduit to control the flow rate of the liquid backwashing the filter membrane 62.

In some embodiments, the filter membrane 62 may be made of a material including, for example, PTFE, PP, PC, nylon, PES, PVDF, or a sintered porous material. The filter membrane 62 may be treated with hydrophilicity and/or positive charge, so that it is not easy to adsorb cells that can block the filter membrane 62. The filter membrane 62 may adopt a variety of pore sizes (including, for example, 0.2 μm, 1 μm, 4 μm, 5 μm, 10 μm, 20 μm, 50 μm, 200 μm, etc.) according to different biological processes (such as stem cells, tumor cells, CHO cells, microcarrier processes, etc.). The support plate 83 may be made of a material including, for example, PS, PMMA, PETG, PET and any other mesh material, or may be a machined product of these materials. The support plate 83 may be configured as a single layer or multiple layers.

The operation process of the disposable cell separation apparatus 2 according to the first embodiment of the present disclosure may be described below. In some embodiments, the flow direction of the liquid may be cyclic, i.e., the outflow of the liquid in the bioreactor 2 and the inflow of the liquid to the bioreactor 2 may be conducted by two pipelines, and the liquid in each pipeline may flow in one direction. First, as shown in FIG. 3A, the inlet valve 52L may be opened, the outlet valve 53L may be closed, the power device 3 may suction gas out from the liquid cavity 40L, and thus, the liquid in the bioreactor 1 may be suctioned into the liquid cavity 40L. After the liquid reaches a preset scale of the liquid cavity 40L, the inlet valve 52L may be closed and the outlet valve 53L may be opened. As shown in FIG. 3B, the power device 3 may reverse and use a positive pressure to push the liquid out from the liquid cavity 40L, and push the liquid to the filter device 6 through the liquid channel 73L. The liquid may serpentinely flow in the tortuous filter channel 61, be filtered through the filter membrane 62, and enter the collection chamber 63. Finally, the filtered liquid may be drained through the return conduit 65.

The operating states of the inlet valve 52R and outlet valve 53R on the side of the liquid cavity 40R may be exactly opposite to those of the inlet valve 52L and the outlet valve 53L on the side of the liquid cavity 40L. As shown in FIG. 3A, when the power device 3 suctions the liquid into the liquid cavity 40L through a negative pressure, the inlet valve 52R may be closed and the outlet valve 53R may be opened, and the power device 3 may use a positive pressure to push the liquid out from the liquid cavity 40R, and reach the filter device 6 through the liquid channel 73R. The liquid may serpentinely flow in the tortuous filter channel 61, be filtered through the filter membrane 62, and enter the collection chamber 63. Finally, the filtered liquid may be drained through the return conduit 65. As shown in FIG. 3B, when the power device 3 uses a positive pressure to push the liquid out from the liquid cavity 40L, the inlet valve 52R may be opened and the outlet valve 53R may be closed, and the power device 3 may use a negative pressure to suction gas out from the liquid cavity 40R, and thus, the liquid in the bioreactor 1 may be suctioned into the liquid cavity 40R by using a negative pressure.

The liquid cavities 40L and 40R may cooperate with each other repeatedly and periodically, so that the liquid can be continuously pumped from the bioreactor 1 to the filter device 6. Compared with the reciprocating movement of a single liquid cavity, the using of the two liquid cavities may make the flow in the entire pipeline smooth without generating back and forth pressure fluctuations.

Figure 10:
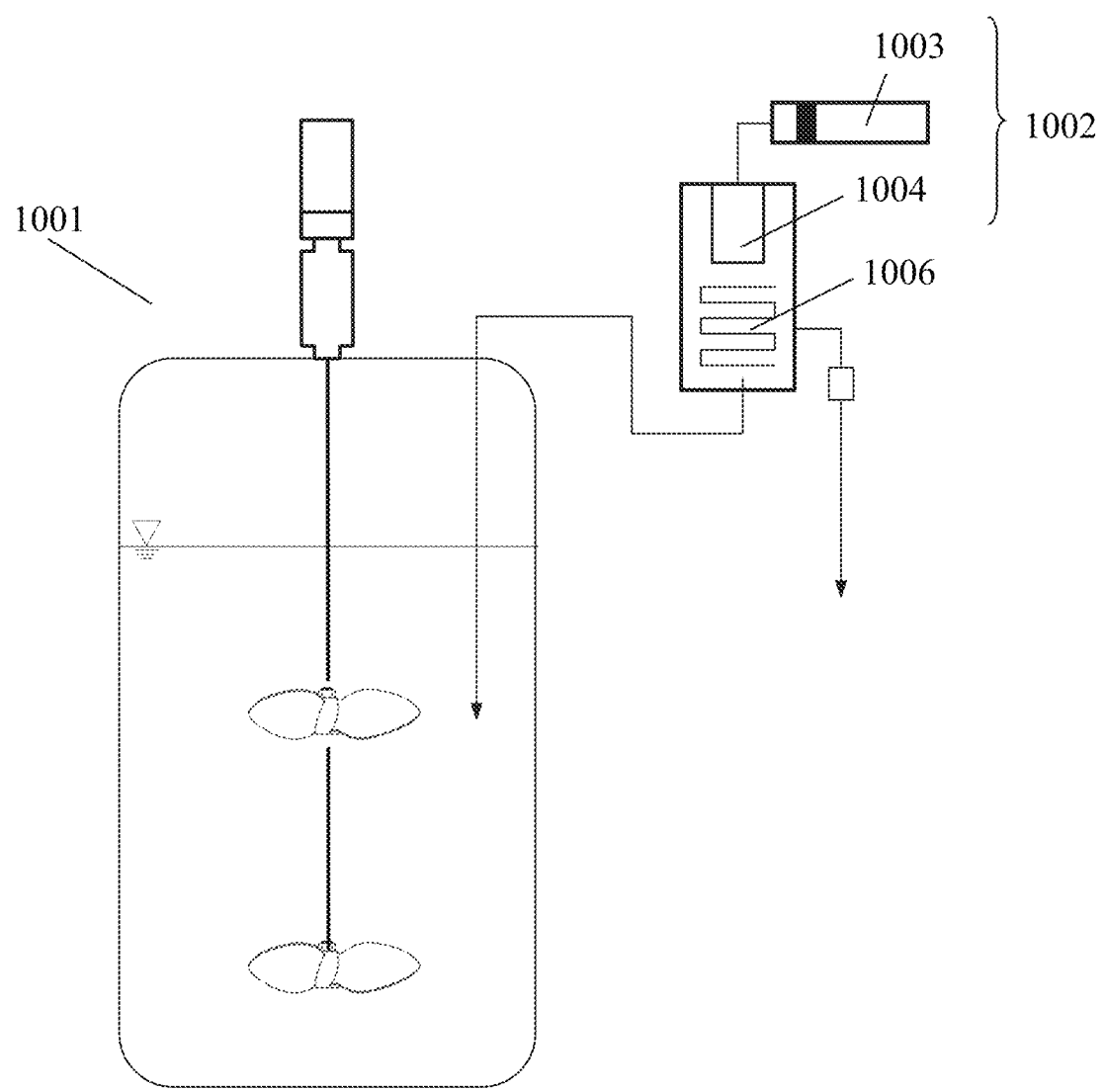
FIG. 10 is a schematic diagram illustrating usage of the disposable cell separation apparatus according to the second embodiment of the present disclosure.
Figure 11A:
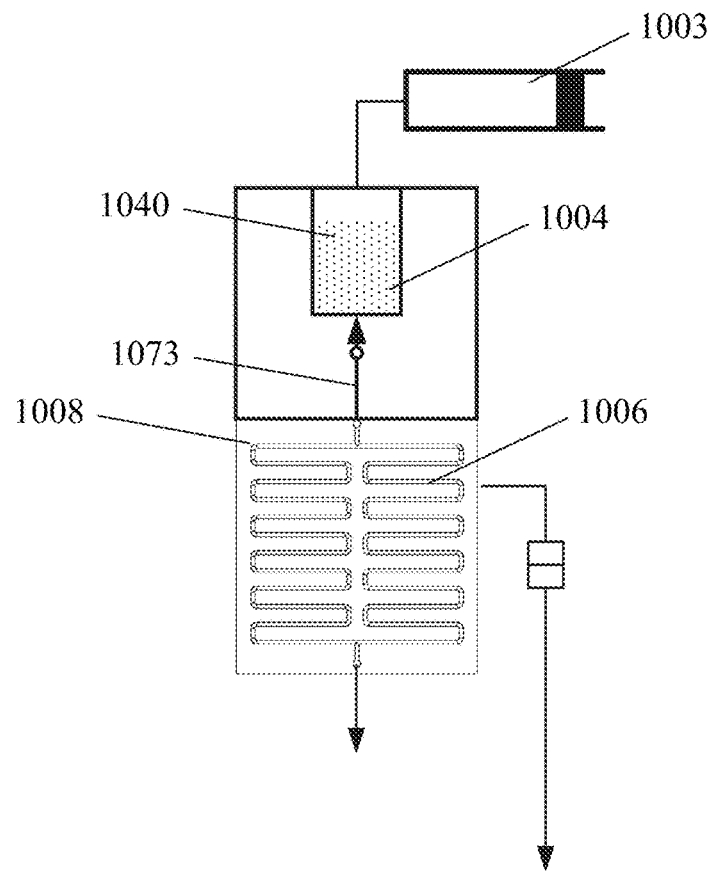
FIGS. 11A and 11B are schematic diagrams illustrating connections of the components of the disposable cell separation apparatus shown in FIG. 10.
Figure 11B:
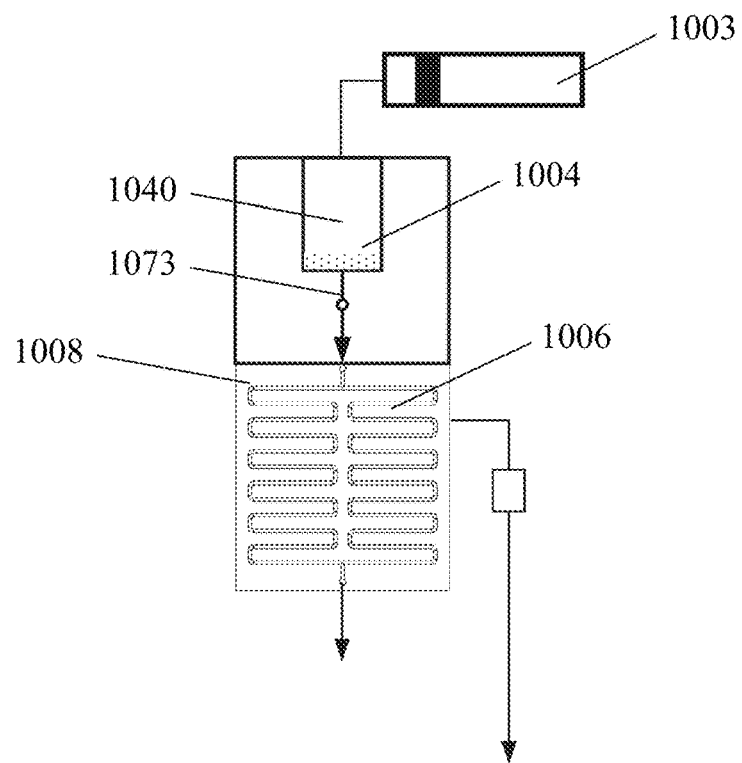

Hereinafter, a schematic diagram of a disposable cell separation apparatus 1002 according to a second embodiment of the present disclosure will be described with reference to FIGS. 10, 11A, and 11B. The cell separation apparatus 1002 may indicate the same or similar structure in the cell separation apparatus 2. The reference number of the cell separation apparatus 2 plus 1000 may correspond to a reference number of the cell separation apparatus 1002. The cell separation apparatus 1002 may include a liquid buffer device 1004 and a filter device 1006. The filter device 1006 and the bioreactor 1001, and the liquid buffer device 1004 and the filter device 1006 may be in fluid connection through one or more liquid pipelines. The power device 1003 and the liquid buffer device 1004 may be in fluid connection through one or more gas pipelines. The power device 1003 may be configured to drive the liquid to leave the bioreactor 1001, and enter the liquid buffer device 1004 and the filter device 1005, and finally be discharged.

The liquid buffer device 1004 and the filter device 1006 may be integrated on the box body 1008, and be disposed from a first end of the box body 1008 to an opposite second end. The liquid buffer device 1004 and the filter device 1006 may be in a fluid connection through a liquid pipeline disposed on the box body 1008. The power device 1003 may be fixed to a first end of the box body 1008 by various known methods (such as screw connection, welding, shape matching, etc.), and be in fluid connection with the liquid buffer device 1004.

The liquid buffer device 1004 may include a single liquid cavity 1040 disposed near the first end of the box body 1008.

The liquid cavity 1040 may receive liquid inside the cavity. In some embodiments, the liquid cavity 1040 may be of a rectangular parallelepiped or a cube shape, and include an inner wall facing the valve device 1005 and the filter device 1006, an opposite outer wall, and a side wall connecting the inner wall and the outer wall.

The liquid cavity 1040 may include one or more air holes disposed on a side wall or an outer wall thereof, and a liquid port disposed on an inner wall thereof. The air holes may be in fluid communication with the power device 1003, and the liquid port may be in fluid communication with the filter device 1006 through a liquid channel 1073 disposed on the box body 1008. Gas (for example, the air) may exist between the power device 1003 and the liquid surface in the liquid cavity 1040. The power device 1003 may suction the gas out from the liquid cavity 1040 through the air holes, and generate a negative pressure in the liquid cavity 1040, thereby suctioning the liquid in the bioreactor 1001 into the liquid cavity 1040 through the filter device 1006, the liquid channel 1073 and the liquid port. The power device 1003 may further push the gas into the liquid cavity 1040 through the air hole(s), and generate a positive pressure in the liquid cavity 1040, thereby discharging the liquid in the liquid cavity 1040 through the liquid port, the liquid channel 1073 and the filter device 1006.

Similar to the box body 8, in addition to the liquid cavity 1040, the box body 1008 may further include a first shell plate, a membrane layer, a support plate, and a second shell plate that stack on each other. A liquid channel 1073, a valve device 1005, and a filter device 1006 may be disposed between the stacked layer. The liquid cavity 1040 may be fixed to an outer end surface of the stacked layer in various ways (for example, by ultrasonic welding, bonding, etc.).

Similar to the liquid channel 73, the liquid channel 1073 may be configured as a micor channel and recessed from an inner surface of the first shell plate, and a top of the liquid channel may be covered and sealed by a sealing film in the membrane layer. An inlet of the liquid channel 1073 may be aligned and connected to the liquid port of the liquid cavity 1040, and an outlet of the liquid channel may be in fluid communication with the filter device 1006. In some embodiments, the liquid channel 1073 may be configured on the first shell plate by mechanical processing, laser etching, soft plastic injection molding, or the like. In some embodiments, a pressure sensor may be installed in the liquid channel 1073 to monitor whether the filter device 1006 is clogged.

The filter device 1006 may include a filter channel, a filter membrane, and a collection chamber. The filter channel may be configured as a microfluidic channel. An inlet of the filter channel may be in fluid connection with the liquid channel 1073 to receive the liquid to be filtered from the liquid cavity 1040. An outlet of the filter channel may be closed or the filter channel may form a closed loop. The structure of the filter device 1006 may be similar to that of the filter device 6 in the first embodiment, and the description will not be repeated herein.

The operation process of the disposable cell separation apparatus 1002 according to the second embodiment of the present disclosure will be described below. In some embodiments, the flow of the liquid may be reciprocating, i.e., the outflow of the liquid in the bioreactor 2 and the inflow of the liquid to the bioreactor 2 may be conducted by a single pipeline, and the liquid in the pipeline may flow in two directions. First, as shown in FIG. 11A, the power device 1003 may suction the gas out of the liquid cavity 1040, and thus, the liquid in the bioreactor 1001 may be suctioned through the filter device 1006 and the liquid channel 1073 to the liquid cavity 1040 by using a negative pressure. After the liquid reaches a preset scale of the liquid cavity 1040, the power device 1003 may reverse and use a positive pressure to push the liquid out from the liquid cavity 1040, and push the liquid through the liquid channel 1073 to the filter device 1006. The liquid may serpentinely flow in the tortuous filter channel, be filtered through the filter membrane, and enter the collection chamber. Finally, the filtered liquid may be drained through the return conduit.

Compared with a traditional cell separation apparatus, the cell separation apparatus according to the embodiments of the present disclosure may include a power system for filtering and micro channels integrated in the cell separation apparatus that is of a box shape, thereby reducing the volume and production cost thereof.

The cell separation apparatus according to the embodiments of the present disclosure may use a gas to generate a driving power and/or a suction power of the liquid, thereby greatly reducing the damage to cells caused by other methods (such as using peristaltic pumps or centrifugal pumps).

The cell separation apparatus according to the embodiments of the present disclosure may reduce the complexity and error-prone nature of the traditional cell separation apparatuses caused by the valve(s) and pipeline connection(s), thereby improving the stability of the system.

The cell separation apparatus according to the embodiments of the present disclosure may utilize the high-speed tangential flow in the micro channel (the pore diameter of the micro channel may be below 2 mm, and the flow rate is as high as 30 cm/s or more), thereby greatly improving the service life of the filter membrane. Because the cells in the pipeline are in laminar flow, the turbulent shear force thereof may have no significant impact on the cells. Because the filtering effect is greatly improved, the cell separation apparatus according to the embodiments of the present disclosure only needs a filter membrane with a very small area, and the manufacturing cost may be greatly reduced with respect to the hollow fiber column.

A micro channel switch may be integrated into the cell separation apparatus according to the embodiments of the present disclosure, and the opening and closing of the microfluidic channel switch may be controlled by a membrane. The switching between the logic of the power system and the multi-channels may be conveniently controlled, thereby making the system flexible.

Although exemplary embodiments of the present disclosure have been described, those skilled in the art should understand that various changes and alterations can be made to the exemplary embodiments of the present disclosure without substantially departing from the spirit and scope of the present disclosure. Therefore, all changes and alterations are included in the protection scope of the present disclosure defined by the claims. The present disclosure is defined by the appended claims, and equivalents of these claims are also included.

We claim:

1. A cell separation apparatus for a bioreactor, the cell separation apparatus being in fluid connection with the bioreactor, the cell separation apparatus being in a shape of a box body, the cell separation apparatus comprising:
 a liquid buffer device including a first liquid cavity disposed in the box body; and
 a filter device including a filter channel and a filter membrane disposed in the box body, the filter membrane being disposed above the filter channel, the filter membrane including a single layer or stacked multiple layers;

a power device fixed to the box body;
wherein a first liquid channel is disposed in the box body to facilitate liquid in the first liquid cavity to flow to the filter channel for filtering, and the first liquid cavity is in gaseous communication with the power device.

2. The cell separation apparatus of claim 1, wherein the power device includes a syringe pump or an air cylinder.

3. The cell separation apparatus of claim 1, wherein a volume ratio of the first liquid cavity to the bioreactor is 0.01-0.8.

4. The cell separation apparatus of claim 1, wherein the box body includes a stacked layer, and the stacked layer includes a first shell plate, a membrane layer, a support plate, and a second shell plate.

5. The cell separation apparatus of claim 4, wherein the first liquid cavity is fixed to an outer end surface of the stacked layer.

6. The cell separation apparatus of claim 4, wherein the first liquid channel is recessed from an inner surface of the first shell plate, and a top of the first liquid channel is covered and sealed by a sealing film in the membrane layer.

7. The cell separation apparatus of claim 6, wherein a pressure sensor is configured in the first liquid channel to monitor a clogging state of the filter device.

8. The cell separation apparatus of claim 6, wherein the first liquid channel is configured on the first shell plate through at least one of machining, laser etching, or soft plastic injection molding.

9. The cell separation apparatus of claim 4, wherein the liquid buffer device further comprises a second liquid cavity disposed in the box body, a second liquid channel is configured in the box body to facilitate a fluid communication between the second liquid cavity and the filter channel.

10. The cell separation apparatus of claim 9, wherein the second liquid cavity is fixed to an outer end surface of the stacked layer.

11. The cell separation apparatus of claim 9, wherein the second liquid cavity is in gaseous communication with the power device.

12. The cell separation apparatus of claim 9, wherein a third liquid channel is configured in the box body to facilitate a fluid communication between the first liquid cavity and the bioreactor, and a fourth liquid channel is disposed in the box body to facilitate a fluid communication between the second liquid cavity and the bioreactor.

13. The cell separation apparatus of claim 12, wherein the first liquid channel, the second liquid channel, the third liquid channel, and the fourth liquid channel are recessed from an inner surface of the first shell, and a top of the first liquid channel, a top of the second liquid channel, a top of the third liquid channel, and a top of the fourth liquid channel are covered and sealed by a sealing film in the membrane layer.

14. The cell separation apparatus of claim 12, wherein one or more pressure sensors are configured in the first liquid channel and/or the third liquid channel to monitor a clogging state of the filter device.

15. The cell separation apparatus of claim 12, wherein the first liquid channel, the second liquid channel, the third liquid channel, and/or the fourth liquid channel are configured on the first shell plate through at least one of machining, laser etching, or soft plastic injection molding.

16. The cell separation apparatus of claim 4, wherein the filter channel is recessed from an inner surface of the first shell plate, and a top of the filter channel is covered by the filter membrane in the membrane layer.

17. The cell separation apparatus of claim 16, wherein an arrangement pattern of the filter channel on the first shell plate is of a coiled shape.

18. The cell separation apparatus of claim 1, wherein the filter channel is configured as a single filter channel, and an outlet of the single filter channel is closed or the single filter channel forms a closed loop.

19. The cell separation apparatus of claim 1, wherein the filter channel is configured as a plurality of filter channels connected in parallel, and an outlet of each filter channel of the plurality of filter channels is closed or the each filter channel forms a closed loop.

20. The cell separation apparatus of claim 4, wherein the cell separation apparatus further comprises an inlet valve disposed in the first liquid channel, and the inlet valve includes a valve body cavity and a spool cavity, wherein the valve body cavity is recessed from an inner surface of the first shell plate, and a top of the valve body cavity is covered and sealed by a sealing film in the membrane layer.

* * * * *